(12) United States Patent
Moore

(10) Patent No.: US 10,661,099 B2
(45) Date of Patent: May 26, 2020

(54) TREATMENT OF ALZHEIMER'S DISEASE

(71) Applicant: Eugene R. Moore, Midland, MI (US)

(72) Inventor: Eugene R. Moore, Midland, MI (US)

(73) Assignee: Eugene R. Moore, Midland, MI (US)

( * ) Notice: Subject to any disclaimer, the term of this patent is extended or adjusted under 35 U.S.C. 154(b) by 654 days.

(21) Appl. No.: 14/999,685

(22) Filed: Jun. 14, 2016

(65) Prior Publication Data

US 2016/0367837 A1 Dec. 22, 2016

Related U.S. Application Data

(60) Provisional application No. 62/230,812, filed on Jun. 16, 2015, provisional application No. 62/284,410, filed on Sep. 29, 2015, provisional application No. 62/388,399, filed on Jan. 28, 2016.

(51) Int. Cl.
| | |
|---|---|
| *A61N 5/10* | (2006.01) |
| *A61B 5/00* | (2006.01) |
| *A61B 5/055* | (2006.01) |
| *A61B 6/03* | (2006.01) |
| *A61B 6/00* | (2006.01) |

(52) U.S. Cl.
CPC ............ *A61N 5/1039* (2013.01); *A61B 5/055* (2013.01); *A61B 5/4082* (2013.01); *A61B 5/4088* (2013.01); *A61B 5/4836* (2013.01); *A61N 5/10* (2013.01); *A61B 5/4076* (2013.01); *A61B 6/032* (2013.01); *A61B 6/501* (2013.01)

(58) Field of Classification Search
CPC .... A61N 5/10–1084; A61N 2005/1003–1098; A61B 5/4082; A61B 5/4088; A61B 5/4836
See application file for complete search history.

(56) References Cited

U.S. PATENT DOCUMENTS 6,008,221 A * 12/1999 Smith .................. A61K 31/505
514/250
2013/0323166 A1 12/2013 Fontanesi et al.

OTHER PUBLICATIONS

"Radiation Dosimetry for CT Protocols," Environmental Health & Safety at Columbia University, http://ehs.columbia.edu/Dosimetry%20Help/CTDoseEstimates.htm, backdated to at least Nov. 8, 2012 via https://web.archive.org/web/20121108161123/http://www.ehs.columbia.edu/Dosimetry%20Help/CTDoseEstimates.htm, retrieved on Oct. 7, 2016.*
"CT Dose Monitoring Policy," Medical Physics Consultants, http://www.mpcphysics.com/documents/MichiganCTDoseMonitoringPolicy3-13-2012.pdf, retrieved on Oct. 7, 2016.*
Bistolfi, "Localized Amyloidosis and Alzheimer's Disease: the Rationale for Weekly Long-Term Low Dose Amyloid-Based Fractionated Radiotherapy," The Neuroradiology Journal 21: 683-692, 2008.*

* cited by examiner

*Primary Examiner* — Thaddeus B Cox
(74) *Attorney, Agent, or Firm* — Technology Law PLLC; Karen L Kimble; Timothy S. Stevens

(57) ABSTRACT

A method for the treatment of a person suffering from neurodegenerative disease such as Alzheimer's, Parkinson's, or Huntington's disease by treating the patient's brain, over the span of one year or less with a plurality of doses of ionizing radiation, each dose being more than 2.5 mJ/kg but less than 150 mJ/kg with the total dose being more than 10 mJ/kg but less than 400 mJ/kg.

17 Claims, 2 Drawing Sheets

TREATMENT OF ALZHEIMER'S DISEASE

The instant application claims priority to the following U.S. Provisional Patent Applications: 62/230,812 filed Jun. 16, 2015; 62/284,410 filed Sep. 29, 2015; and 62/388,399 filed Jan. 28, 2016.

BACKGROUND OF THE INVENTION

The instant invention is in the field of treatments for disease and more specifically, the instant invention is in the field of the treatment of diseases of the brain such as Alzheimer's, Parkinson's, and Huntington's disease, and many others. Alzheimer's disease is a neurodegenerative disease that usually starts slowly and gets worse over time. As the disease advances, symptoms can include: problems with language, disorientation, mood swings, loss of motivation, and behavioral issues. Gradually body functions are loss, ultimately leading to death. No cure, only slowing the loss of function, is seen, even when using the very best available medication. Damage to the brain progresses in spite of the use of the best currently known medications and procedures. Beta-amyloid accumulation as plaque deposits in the brain has usually been blamed for progression of Alzheimer's disease.

Parkinson's is another neurodegenerative disease that can cause slowness in movement, tremors at rest, rigidity, flexed posture, and freezing. It also can cause depression, fatigue, hypotension, constipation, sleep problems, and dementia. It is widely accepted that the presence of a protein called alpha-synuclein is responsible for deposits in the brain associated with the progression of Parkinson's disease.

Huntington's disease is also a neurodegenerative disease, but one that requires a genetic predisposition. It effects about 7 per 100,000 people of Western descent. There is no known method of stopping the disease as it progresses from a general lack of coordination and an unsteady gate to jerky body movements along with a decline in mental abilities. In final stages full-time care is required. The disease appears to result from misfolded fragments of the huntingtin (Htt) protein that form aggregates (inclusions). These accumulating inclusions are believed to be responsible for the progression of the disease.

It appears that many neurodegenerative diseases have the accumulation of "inclusions" in the brain. These inclusions are formed from an evolving failure of the body to dispose of common molecular "waste" products. Up to an advanced age the body's natural protective system is capable of recognizing and disposing of these products. It doesn't seem to matter rather it is the beta-amyloid of Alzheimer's or the alpha-synuclein of Parkinson's, or the Htt protein of Huntington's disease. All of these diseases seem related to a gradual inactivation of the body's natural protective system. This inactivation appears mostly to be of the brain's microglial cells.

Exposure of the brain to ionizing radiation as a possible treatment for Alzheimer's disease is known, see for example US Patent Application Publication 2013/0323166, wherein the total dose administered to the patient ranged from 500 mGy to 18,000 mGy with a daily dose ranging from 500 mGy to 6,0000 mGy. Although this approach removes beta-Amyloid plaque it does not produce recovery of cognizant or physical ability.

SUMMARY OF THE INVENTION

We have surprisingly found that much lower levels of ionizing radiation than the levels disclosed in US Patent Application Publication 2013/0323166 are effective to recover cognizant and/or physical ability. The instant invention is the discovery of a treatment for a neurodegenerative disease such as Alzheimer's, Parkinson's, or Huntington's disease wherein the total dose and the daily dose of ionizing radiation administered to the brain of the patient is much lower than taught by the prior art. More specifically, the instant invention is a method for the treatment of a person suffering from a neurodegenerative disease such as Alzheimer's, Parkinson's, or Huntington's disease by exposing the patient's brain to a plurality of doses of ionizing radiation preferably administered over a period of time, each dose being more than 2.5 millijouls per kilogram of brain weight (mJ/kg) but less than 150 mJ/kg with the total yearly dose being more than about 10 mJ/kg but less than about 400 mJ/kg. The total dose is preferably more than 20 mJ/kg and more preferably more than 40 mJ/kg and perhaps even more preferably more than 80 mJ/kg. However, the total yearly dose is preferably less than 300 mJ/kg and more preferably less than 200 mJ/kg and perhaps even less than 180 mJ/kg.

DETAILED DESCRIPTION OF THE INVENTION

Figure 1:
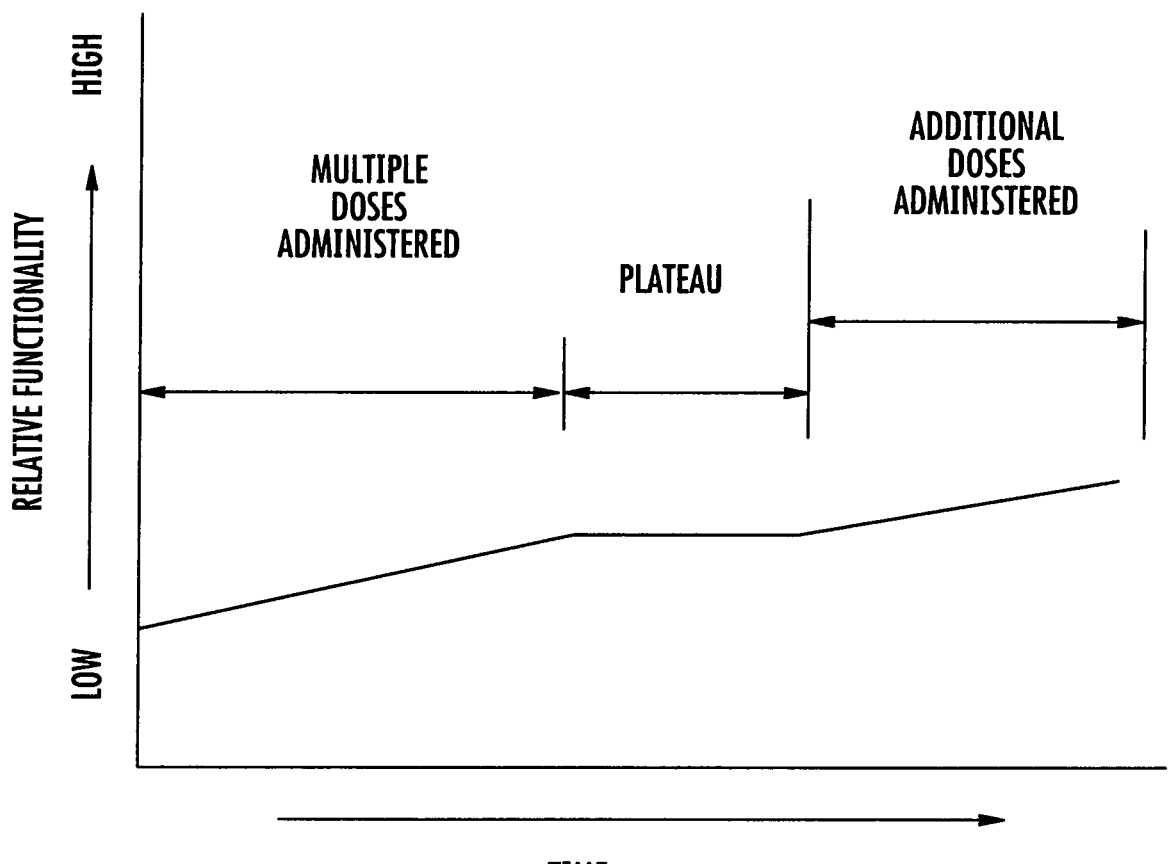
FIG. 1 is a plot of a person's relative functionality v. time after a plurality of doses of ionizing radiation according to a highly preferred embodiment of the instant invention wherein the person's recovery of relative functionality is allowed to plateau before the administration of additional doses of ionizing radiation.

The instant invention is a method for the treatment of a person suffering from a neurodegenerative disease such as Alzheimer's, Parkinson's or Huntington's disease by exposing the patient's brain to a plurality of doses of ionizing radiation, each dose being more than 2.5 mJ/kg but less than about 150 mJ/kg, with the total yearly dose being more than 10 mJ/kg but less than 400 mJ/kg. The total dose is preferably more than 20 mJ/kg and more preferably more than 40 mJ/kg and perhaps even more preferably more than 80 mJ/kg. However, the total yearly dose is preferably less than 300 mJ/kg and more preferably less than 200 mJ/kg and perhaps even less than 180 mJ/kg.

It should be understood that the instant invention comprises treatment after one year and that treatment in a subsequent year or in subsequent years should follow the teachings of this disclosure. The treatment comprises reversing one or more of the clinical symptoms of such disease. In another embodiment, the treatment comprises inhibiting, arresting the development of, or preventing the progression of one or more clinical symptoms of such disease. The period of time between doses is preferably more than a week and more preferably a month or a number of months. When the treatment is directed to the reversal of one or more of the clinical symptoms of Alzheimer's, Parkinson's, or Huntington's disease, then the time between the doses of ionizing radiation is preferably determined by measuring a plateau in the reversal of one or more of the clinical symptoms of Alzheimer's, Parkinson's, or Huntington's disease before the next dose is administered. The term "plateau" refers to a plurality of determinations of the clinical symptoms of neurodegenerative disease such as Alzheimer's, Parkinson's, or Huntington's disease over time showing an observed leveling of improvement in said clinical symptoms. Said clinical symptoms can be determined by a one of the following techniques. Use of observations by workers, family members, and friends is perhaps the easiest but most subjective technique. If the patient is in earlier to mid-stage of a neurodegenerative disease such as Alzheimer's, Parkinson's, or Huntington's there are mini-tests having only about 30 questions that are more quantitative. A neuropsychological exam carried out by a professional is even more quantitative. There are a variety of imaging tests such as MRI or CT scans that look directly at changes in the brain morphology associated with advancement of Alzheimer's disease (AD), or in this case, recovery from AD. Positron Emission Tomography (PET) provides a technique to measure the amount of beta-Amyloid plaque being removed from, or deposited in the Alzheimer's patient's brain. Similarly for the alph-synuclean of Parkinson's disease. This test is slightly invasive since a radioactive tracer is used as a tagging compound for the beta-amyloid. This tracer must be injected into the blood and allowed to deposit on the amyloid plaque. There are chemical markers in the blood that indicate the "health" of the brain. These chemical markers may be used to indicate when to best give the next immune simulation CT scan or other exposure to low doses of ionizing radiation. Blood markers such as the level of the Y Chromosome (the loss of which is related to progression of Alzheimer's disease) can be used in the instant invention. Other tests will be obvious to those skilled in the art of measuring brain and physical function.

The ionizing radiation of the instant invention is preferably of a selected energy or energy range to maximize absorption of the energy within the brain of the patient and to minimize over-penetration or under-penetration. The term "treatment" used herein comprises: (a) reversing one or more clinical symptoms of neurodegenerative disease such as Alzheimer's, Parkinson's, or Huntington's disease; (b) inhibiting, arresting the development of, or preventing the progression of one or more clinical symptoms of neurodegenerative disease such as Alzheimer's, Parkinson's, or Huntington's disease; and (c) preventing the occurrence of neurodegenerative disease such as Alzheimer's, Parkinson's, or Huntington's disease. The term "ionizing radiation" is defined herein as including but not limited to x-ray, gamma ray, or proton beam energy absorbed expressed in millijoules per kilogram weight of brain tissue contained within the skull of the patient. 1 mJ/kg is equal to 1 mGy or 1 mSv. The action of absorbed ionizing radiation is believed to activate the brains natural protective system which includes the immune system. The immune part of this protective system has been identified as the Microglial cells which have been said to be up to 15% of all cells in the brain. Normally these cells would protect the brain from the excess accumulation of either beta-amyloid, alpha-synuclein, or huntingtin (Htt) "inclusions". As a person ages, however, these natural protective mechanisms become less active and allow destructive compounds such as "plaques" of beta-amyloid, alpha-synuclein, or Htt to accumulate. Even more important than the action of ionizing radiation on destruction of beta-amyloid or alpha-synuclein or Htt, is the rate of destruction of these "space occupying" compounds. It is believed that the brain requires time to, for want of a better term, "backfill" or "heal" around the vacancies created by the destruction of the beta-amyloid, alpha-synuclein, or Htt. If they are removed too rapidly the desired return of cognitive function may not take place.

It is believed that there will be variations from patient to patient in the amount of ionizing radiation required to activate the body's natural protective system (or Microglial) up to the effective range. This right amount must be approached with the understanding that proceeding slowly is recommended and that proceeding too rapidly may result in failure. It is, of course desired to recover from neurodegenerative diseases as rapidly as practical. Attempting to recover too rapidly may, however, cause inadvertent damage that will limit the recovery of cognitive function. As with any new, ground breaking, treatment by medical practitioners, caution is recommended.

Figure 2:
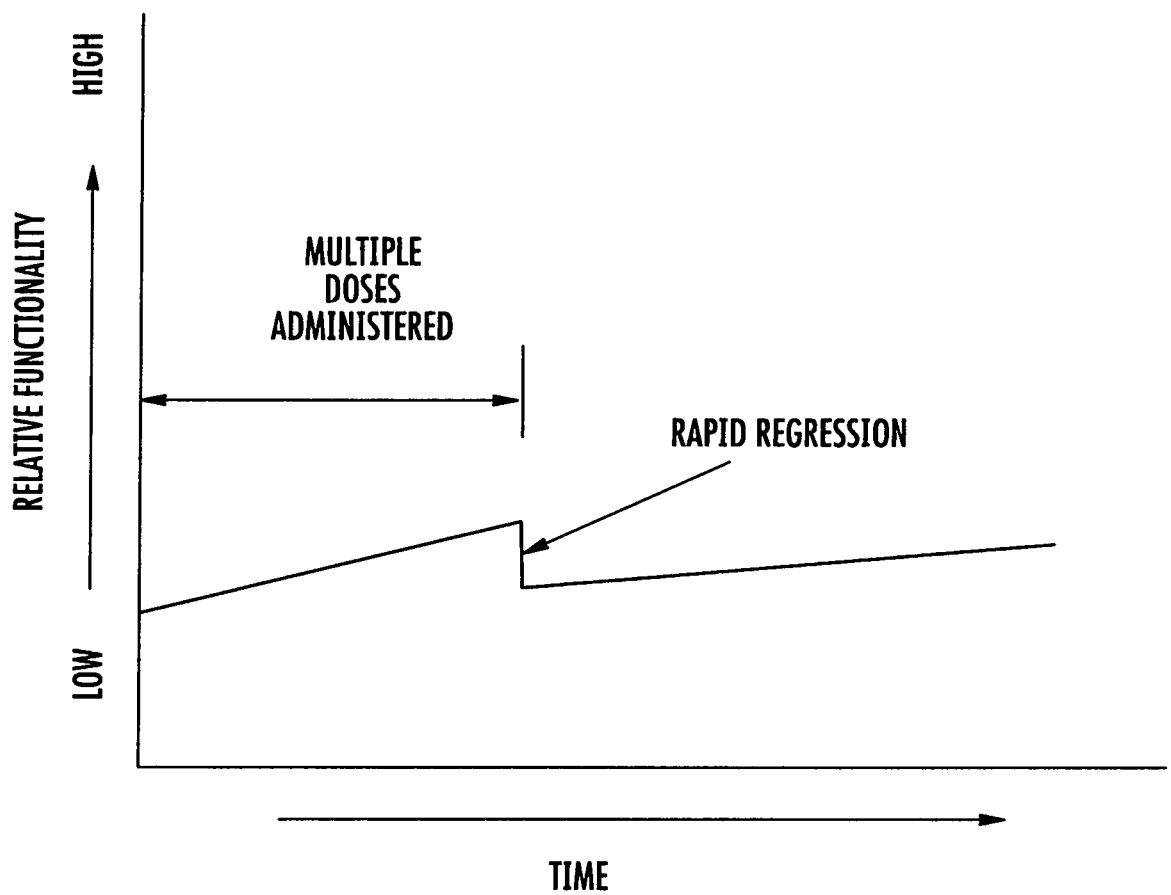
FIG. 2 is a plot of a person's relative functionality v. time wherein the number of doses of ionizing radiation over a period of time results in rapid regression of the person's relative functionality followed by a slow recovery of the person's relative functionality.

It appears desirable to not have an additional CT scan, or other application of ionizing radiation, while there is continuing improvement. When other tests are not available this improvement is measured subjectively, preferably involving more than one person's opinion. Early stage progress may be followed with a variety of cognitive tests, some as simple as the 30 questions mini-tests. There are many other more formal tests that can be used when available. The use of MRI's will show progressive changes in the brain structure and would be a preferred technique along with CT scans of effective areas of the brain such as the hippocampus area. Blood markers may be used to show changes in blood chemistry. Positron emission Tomography (PET) can be used with markers that, when injected, attach to beta-amyloid plaque and are detectable. Other tests will be obvious to those skilled in the art of measuring brain and physical function. FIGS. 1 and 2 show this graphically. In FIG. 1 the preferred approach is shown, where a slow but steady increase in function is observed and then a significant plateau is seen and then an additional CT scan is delivered and improvement continues. FIG. 2 shows the effect of delivering the next CT scan too early, with a substantial regression in relative functionality.

The use of CT scans to supply the ionizing radiation is preferred at the time of the filing of this application. CT scans have the necessary governmental approval, are readily available in almost all developed countries, and are widely known and accepted in common medical practice. In the future it is believed that those skilled in the art of X-ray equipment design and manufacture will easily produce very much less complex, more portable, and lower cost equipment to deliver the selected treatment. This equipment may deliver x-rays from a stationary source or from a circling source. This equipment will cover needs where CT scan equipment is not yet existing or is not able to meet the demand. In addition, there will be the need for the desired ionizing radiation treatment of this invention in areas where delivery is not possible by either CT scans or simple x-ray equipment. Such equipment and required supporting infrastructure may not reasonable be available. For those cases, a wide variety of isotopes with appropriate shielding and shutters could be used to extend the benefits of this invention to needy humans anywhere in the world. In some cases a "dose" may be delivered over an extended period of time. This might be done, for example, with a very low dose x-ray type equipment, or a very low radiation emitting source such as uranium or radium ore, partially enriched ore, diluted spent fuel, etc.

EXAMPLES

Example 1

This example demonstrates the surprising and beneficial effect of low level exposure of an Alzheimer's patient's brain to ionizing radiation. The brain of a patient with advanced Alzheimer's disease is exposed to ionizing radiation. The exposure is carried out using a megavoltage linear accelerator. The energy is chosen to produce a uniform dose distribution across the brain. The dose for each field is verified through a second check dose calculation prior to treatment. The dose is verified during treatment by measuring the dose at the entrance point. The dose is 20 mJ/kg per treatment, two weeks apart for the first four treatments. After the first four treatments the remaining treatments are given at monthly intervals. The total dose of about 200 mJ/kg is given. A PET scan, targeting beta-amyloid, performed before and after the exposure shows significant reduction in the beta-amyloid plaque. There is a detectable improvement in memory function of the patient after four weeks with steady and continued improvement seen for more than one year.

Example 2

Example 1 is repeated except the ionizing radiation exposure is given by a series of standard CT scans to deliver about 40 mJ/kg per treatment for a total of 400 mJ/kg. Similar beneficial results are seen.

Example 2a

Example 1 is repeated except the ionizing radiation is given by a series of exposures delivered by a cobalt 60 source, with similar beneficial results.

Example 2b

Example 1 is repeated except the ionizing radiation is delivered by a series of exposures is given by a spent nuclear fuel source, with similar beneficial results.

Example 2c

Example 1 is repeated except the ionizing radiation is delivered by simple X-ray equipment having no imaging capability, with similar beneficial results.

Example 2d

Example 1 is repeated except the ionizing radiation is delivered by a much diluted cobalt 60 source placed under the head of the patient's mattress. The dilution is such that the patient receives about 40 mJ/kg of exposure over a 5 day period while spending an average of 8 hours sleeping. Similar beneficial results are seen.

Example 3

This example demonstrates the hazards of delivering radiation outside the limits of our invention. As in Example 2 above, the brain of a patient with advanced Alzheimer's disease is exposed to ionizing radiation. The exposure, however, is 200 mJ/kg per day for 8 days in a row so that the total dose is 1600 mJ/kg. A PET scan before and after the exposure shows significant reduction in the beta-amyloid plaque but there is no detectable improvement in memory function. This exposure is shown to be above the level that effectively restores brain function and is given too rapidly.

Example 4

An 81 year old female with advanced stage Alzheimer's disease is treated with a total of about 160 mJ/kg ionizing radiation using a series of four CT scans of about 40 mJ/kg (40 mGy) given two weeks apart. Improvement is seen after each scan and is still continuing after more than 50 days. During this treatment time she progressed from no coherent speech and severe immobility to a condition of gradually developing more coherent speech and more comprehension of her surroundings. She also shows some 10 year old memory returning and begins to respond again to physical directions. This surprising low ionizing radiation level required may well relate to activation of the bodies natural protective system which appears to involve microglial cells (which are said to be the brain's immune system). After a fifth 40 mJ/kg treatment, given 5½ weeks later, an undesirable, rapid loss in cognitive function is seen. This loss is followed by a gradual return of cognitive function over several months. PET scans using radio nuclide "tracers" that are attracted to beta-amyloid plaque indicate a significant reduction in plaque. This reduction is seen when the PET scans taken several months after the last treatment are compared to those taken prior to the first CT scan. MRI scans taken before and after treatment show favorable changes in brain structure. These changes are indicative of improved cognitive function. The actual doses in mGy are shown below (note 1 mGy is equivalent to 1 mJ/kg). The CTDIvol are doses measured in a plastic patient model and are used as a reference for patient dose. They are the doses that are output by the scanner. The doses in CTDIvol, mGy are calculated to be: scan one and two, 82.3 mGy total; scan three, 38.7 mGy; scan four 46.9 mGy; and scan five 38.5 mGy.

Example 4AA

This example serves to demonstrate that there is a synergistic action with some common AD medication and exposure to low levels of ionizing radiation. This standard medical treatment by itself is found to only slightly slow the progress of the disease but in no case is it found to reverse the debilitation of the disease. Example 4 is repeated except the patient is continued on a common variety of AD medications which include the popular NAMENDA brand memantine hyrrochloride and ARICEPT brand donepezil. Surprisingly, the patient recovery is seen to be superior to that in example 4. It appears that the combination of common AD medication and the treatment of our invention are synergistic and the result of combining the two is superior to the use of either separately.

Example 4A

This example demonstrates desirability of allowing improvements to level (thereby preventing the progression of Alzheimer's disease) before applying an additional exposure to ionizing radiation. Example 4 is repeated except the fifth 40 mJ/kg treatment is delayed until it is observed by a combination of workers, family members, and friends for several weeks that improvement in both mental and physical capability has leveled and reached a plateau. After the treatment a continued improvement in both cognitive and physical ability is seen.

Example 4B

Example 4A is repeated except an earlier stage Alzheimer's patient is treated with only two 40 mJ/kg doses In this case a mini-test involving 30 questions is used to determine that a plateau has been reached before treating with and

Example 4C

Example 4B is repeated with a similar earlier stage Alzheimer's patient who is treated with only two 40 mJ/kg. In this case a neuropsychological exam carried out by a professional is used to determine that a plateau has been reached before treating with and additional 40 mJ/kg. After the treatment a continued improvement in both cognitive and physical ability is seen.

Example 4E

Example 4A is repeated except a series of MRIs are used to determine that a plateau is reached before treating with and additional 40 mJ/kg. After the treatment a similar continued improvement in both cognitive and physical ability is seen.

Example 4F

Example 4A is repeated except a series PET scans are used to determine that a plateau is reached before treating with and additional 40 mJ/kg. After the treatment a similar continued improvement in both cognitive and physical ability is seen.

Example 4G

Example 4A is repeated except a series of CT scans that look directly at changes in the brain morphology associated with advancement of AD, or in this case recovery from AD, are used to determine that a plateau is reached before treating with and additional 40 mJ/kg. After the treatment a similar continued improvement in both cognitive and physical ability is seen.

Example 4G1

This example will serve to demonstrate the particular effectiveness of following the morphology of the hippocampus area of the brain in detecting the plateau in improvements designed to indicate the need for an additional exposure to about 40 mJ/kg of ionizing radiation. As in example 4G a series of CT scans that look directly at changes in the brain morphology in the hippocampus area associated with advancement of AD, or in this case recovery from AD, are used to determine that a plateau is reached before treating with an additional 40 mJ/kg. After the treatment a similar continued improvement in both cognitive and physical ability is seen.

Example 4H

Example 4A is repeated except a series measures of the Y Chromosome is used as a "blood marker" to determine that a plateau is reached before treating with and additional 40 mJ/kg. After the treatment a similar continued improvement in both cognitive and physical ability is seen.

Example 4a

Example 4 is repeated except the CT scans are given at monthly intervals. The results are similar but somewhat better.

Example 4b

Example 4a is repeated except the CT scans are given two months apart. The results are again somewhat better.

Example 4c

Example 4a is repeated except A 55 year old female with middle stage Alzheimer's disease is treated with CT scans and the CT scans are given at intervals of three months. The results are again somewhat better.

Example 4d

Example 4b is repeated except a 65 year old male with early stage Alzheimer's disease is treated with CT scans. The beneficial results are similar.

Example 4e

CT scan equipment is very costly, partly because of the precise positioning and computer interpretation requirements to produce precise images. Simple x-ray equipment, without the complex positioning equipment and computer interface is used to provide the ionizing radiation exposure in a manner similar to Example 4A. The desired therapeutically benefit is again seen.

Example 4f

Example 4e is repeated except the ionizing radiation is supplied by a Cobalt 60 source. Similar beneficial results are seen.

Example 4g

Example 4f is repeated several times using a variety of gamma ray emitting materials, including material that has been used as nuclear power plant fuel. In all cases similar beneficial results are seen.

Example 4h-1

Example 4 is repeated, except during the recovery phase the patient is treated with speech therapy. This therapy is surprisingly shown to help in recovery of speech capability. This therapy consisted of an intensive variety of techniques that have in the past have been used for patients recovering from conditions caused by, for example, strokes or brain injury. Techniques used involved a combination of Copy and Recall Therapy (CART); Visual Action Therapy (VAT); Functional Communication Therapy (FCT); Promoting Aphasic's Communication Effectiveness (PACE); Melodic Intonation Therap (MIT); and others such as "drawing as a way of communicating", "trained conversation partners"; etc. These techniques of treating victims of Alzheimer's disease may have been tried before but have never been reported as successful. It appears that these speech enhancement techniques can only be successful when practiced in conjunction with the treatments of this invention. This invention is the very first time that Alzheimer's disease has actually been reversed in a human. There have been many successes with mice but none have successfully been translated to humans.

Example 4h-2

Example 4h-1 is repeated except the patient has not been treated with any CT scans prior to being treated with the intense speech therapy of Example 4h-1. None of the speech therapy techniques are found to stop or reverse the continual decline in speech capability. The therapy is found to only be effective when the patient is first treated with CT scans.

Example 4j

This example involves treatment of a middle aged male patient with musical talent. He is diagnosed with early stage Alzheimer's and is having trouble reading music. He is given the Folstein Min Mental Status exam on Feb. 22, 2016 and scores 22 out of 30. On Apr. 7, 2016 he is given a CT scan of the brain involving 46.47 mJ/kg of energy. On Apr. 8, 2016 his piano playing Jazz partner comments that he is having a much stronger performance overall, especially in reading of the score and conversation about the music. By Apr. 16, 2016 his wife notes that there is an improvement in his clarity of mind, reading aloud, and his conversational ability. On Apr. 28, 2016 he repeats the Folstein Min Mental Status Examination and increases his score to 24 out of 30. A single CT scan shows a very impressive series of improvements over a very short period of time. After several weeks a leveling or even a slight recession in the improvement is seen. At that time a series of three CT scans are given at two week intervals. Continuation of improvement is then seen. Eventually a stage of near full recovery is attained. In order to retain the recovered benefit it is seen that a continued dose of about 160 mJ/kg or more is administered each year. This dose is administered either quarterly or monthly and is found to maintain the patient's cognitive ability for an extended period of time. This represents yet another example of reversal of Alzheimer's disease in a human which is unique and happens due to the practice of this invention. Others have only shown reversals in mice that have not been reproduced in humans.

Example 4k

This example demonstrates the preventative nature of the process of this invention. A middle aged female hair stylist reports that every one of her female ancestors has died from AD. As she approaches the age where AD began with her ancestors. A continuing dose of about 160 mJ/kg or more is administered each year. This dose is administered either quarterly or monthly and is found to maintain the patient's cognitive ability.

Example 5

An 82 year male with early stage Parkinson's disease has developed a significant tremor, has completely loss the sense of smell, has constipation problems, and suffers from fatigue. The tremor is only partly controlled by six doses/day of the medicine carbidopa-levodopa (25 mg/100 mg) and all symptoms continue to worsen. He is treated with a single CT scan of about 40 mJ/kg ionizing radiation scan. First there is a dramatic reduction of the tremor at 6 doses/day of the carbidopa-levodopa (25 mg/100 mg). Over a period of weeks, the carbidopa-levodopa (25 mg/100 mg) is reduced to three per day. Tremors are noted to be almost absent, only appearing when tired or in an otherwise stressful situation. Other symptoms of Parkinson's are seen to continue to improve. A second scan is given several weeks later and continued improvement is observed.

Example 6

A patient with Huntington's disease is treated with a total of 80 mJ/kg ionizing radiation to the brain using two CT scans given six weeks apart and is seen to have benefited significantly in the same manner as is seen in Example 5.

Example 7

An older dog is diagnosed with Degenerative Myelopathy, he is treated with a series of four whole body CT scans alternating with four CT scans of the brain. The second scan is given two weeks after the first then the remaining at monthly intervals. Improvements in the dog's ability to control movement of his limbs is seen.

Example 8

An older adult male that has suffered for many years of multiple sclerosis. He is alternately given a CT scan of the brain then of the pelvic and chest area two weeks apart. After several cycles, with a total yearly exposure of about 400 mJ/kg, major improvements are seen.

CONCLUSION

While the instant invention has been described above according to its preferred embodiments, it can be modified within the spirit and scope of this disclosure. This application is therefore intended to cover any variations, uses, or adaptations of the instant invention using the general principles disclosed herein. Further, the instant application is intended to cover such departures from the present disclosure as come within the known or customary practice in the art to which this invention pertains.

What is claimed is:

1. A method for a treatment of a person suffering from neurodegenerative disease such as Alzheimer's, Parkinson's, or Huntington's disease, the method comprising: irradiating the person's brain with a plurality of doses of ionizing radiation, each dose being greater than 2.5 mJ/kg but less than 150 mJ/kg for a total dose over a period of time of a year or less being greater than 10 mJ/kg but less than 400 mJ/kg, wherein the treatment is reversing one or more clinical symptoms of Alzheimer's, Parkinson's, or Huntington's disease, wherein there is a period of time between the plurality of doses of ionizing radiation, which period of time is determined by measuring a plateau in the reversal of one or more of the clinical symptoms of Alzheimer's, Parkinson's, or Huntington's disease.

2. The method of claim 1, wherein the total dose is greater than 20 mJ/kg.

3. The method of claim 1, wherein the total dose is greater than 40 mJ/kg.

4. The method of claim 1, wherein the total dose is greater than 80 mJ/kg.

5. The method of claim 1, wherein the total dose is less than 300 mJ/kg.

6. The method of claim 1, wherein the total dose is less than 180 mJ/kg.

7. The method of claim 1, wherein the plurality of doses of ionizing radiation are a plurality of CT scans.

8. The method of claim 1, wherein the plurality of doses of ionizing radiation are delivered by a megavoltage linear accelerator.

9. A method for a treatment of a person suffering from neurodegenerative disease such as Alzheimer's, Parkinson's, or Huntington's disease, the method comprising: irradiating the person's brain with a plurality of doses of ionizing radiation, each dose being greater than 2.5 mJ/kg but less than 150 mJ/kg for a total dose over a period of time of a year or less being greater than 10 mJ/kg but less than 400 mJ/kg, wherein the plurality of doses of ionizing radiation are delivered by simple x-ray equipment having no imaging capability.

10. A method for a treatment of a person suffering from neurodegenerative disease such as Alzheimer's, Parkinson's, or Huntington's disease, the method comprising: irradiating the person's brain with a plurality of doses of ionizing radiation, each dose being greater than 2.5 mJ/kg but less than 150 mJ/kg for a total dose over a period of time of a year or less being greater than 10 mJ/kg but less than 400 mJ/kg, wherein plurality of doses of ionizing radiation are generated from cobalt 60.

11. A method for a treatment of a person suffering from neurodegenerative disease such as Alzheimer's, Parkinson's, or Huntington's disease, the method comprising: irradiating the person's brain with a plurality of doses of ionizing radiation, each dose being greater than 2.5 mJ/kg but less than 150 mJ/kg for a total dose over a period of time of a year or less being greater than 10 mJ/kg but less than 400 mJ/kg, wherein the plurality of doses of ionizing radiation are generated from spent nuclear fuel.

12. A method for a treatment of a person suffering from neurodegenerative disease such as Alzheimer's, Parkinson's, or Huntington's disease, the method comprising: irradiating the person's brain with a plurality of doses of ionizing radiation, each dose being greater than 2.5 mJ/kg but less than 150 mJ/kg for a total dose over a period of time of a year or less being greater than 10 mJ/kg but less than 400 mJ/kg, wherein there is a period of time between the plurality of doses of ionizing radiation, which period of time is determined by measuring a plateau in morphology of the hippocampus area of the brain as determined by a CT scan image of the hippocampus area of the brain.

13. A method for a treatment of a person suffering from neurodegenerative disease such as Alzheimer's, Parkinson's, or Huntington's disease, the method comprising: irradiating the person's brain with a plurality of doses of ionizing radiation, each dose being greater than 2.5 mJ/kg but less than 150 mJ/kg for a total dose over a period of time of a year or less being greater than 10 mJ/kg but less than 400 mJ/kg, wherein there is a period of time between the plurality of doses of ionizing radiation, which period of time is determined by measuring a plateau in a morphology of the hippocampus area of the brain as determined by an MRI scan of the hippocampus area of the brain.

14. A method for a treatment of a person suffering from neurodegenerative disease such as Alzheimer's, Parkinson's, or Huntington's disease, the method comprising: irradiating the person's brain with a plurality of doses of ionizing radiation, each dose being greater than 2.5 mJ/kg but less than 150 mJ/kg for a total dose over a period of time of a year or less being greater than 10 mJ/kg but less than 400 mJ/kg, wherein there is a period of time between the plurality of doses of ionizing radiation, which period of time is determined by measuring a plateau in blood chemistry markers associated with neurodegenerative disease.

15. A method for a treatment of a person suffering from neurodegenerative disease such as Alzheimer's, Parkinson's, or Huntington's disease, the method comprising: irradiating the person's brain with a plurality of doses of ionizing radiation, each dose being greater than 2.5 mJ/kg but less than 150 mJ/kg for a total dose over a period of time of a year or less being greater than 10 mJ/kg but less than 400 mJ/kg, wherein there is a period of time between the plurality of doses of ionizing radiation, which period of time is determined by measuring a plateau in a morphology of the hippocampus area of the brain as determined by a PET scan of the brain.

16. A method for a treatment of a person suffering from neurodegenerative disease such as Alzheimer's, Parkinson's, or Huntington's disease, the method comprising: irradiating the person's brain with a plurality of doses of ionizing radiation, each dose being greater than 2.5 mJ/kg but less than 150 mJ/kg for a total dose over a period of time of a year or less being greater than 10 mJ/kg but less than 400 mJ/kg, wherein there is a period of time between the plurality of doses of ionizing radiation, which period of time is determined by measuring a plateau in a score of a Folstein Mini-Mental State Examination of the person.

17. A method for a treatment of a person suffering from neurodegenerative disease such as Alzheimer's, Parkinson's, or Huntington's disease, the method comprising: irradiating the person's brain with a plurality of doses of ionizing radiation, each dose being greater than 2.5 mJ/kg but less than 150 mJ/kg for a total dose over a period of time of a year or less being greater than 10 mJ/kg but less than 400 mJ/kg, wherein there is a period of time between the plurality of doses of ionizing radiation, which period of time is determined by measuring a plateau in neuropsychological testing of the person.

* * * * *